US010864103B2

United States Patent
Lee

(10) Patent No.: US 10,864,103 B2
(45) Date of Patent: Dec. 15, 2020

(54) VEST-TYPE MATERNITY BELT

(71) Applicant: Eun Sung Lee, Seoul (KR)

(72) Inventor: Eun Sung Lee, Seoul (KR)

( * ) Notice: Subject to any disclaimer, the term of this patent is extended or adjusted under 35 U.S.C. 154(b) by 419 days.

(21) Appl. No.: 15/575,443

(22) PCT Filed: Nov. 11, 2015

(86) PCT No.: PCT/KR2015/012126
§ 371 (c)(1),
(2) Date: Nov. 20, 2017

(87) PCT Pub. No.: WO2016/195184
PCT Pub. Date: Dec. 8, 2016

(65) Prior Publication Data
US 2018/0161191 A1 Jun. 14, 2018

(30) Foreign Application Priority Data

Jun. 5, 2015 (KR) ........................ 10-2015-0079705

(51) Int. Cl.
*A61F 5/03* (2006.01)
*A41C 1/10* (2006.01)
*A44B 13/00* (2006.01)

(52) U.S. Cl.
CPC .................. *A61F 5/03* (2013.01); *A41C 1/10* (2013.01); *A44B 13/0052* (2013.01)

(58) Field of Classification Search
CPC .... A61F 5/03; A61F 5/02; A61F 5/022; A61F 5/024; A61F 5/026; A61F 5/028;
(Continued)

(56) References Cited

U.S. PATENT DOCUMENTS

| | | | | |
|---|---|---|---|---|
| 1,276,410 A | * | 8/1918 | Pratt ........................ | A41C 1/10 450/155 |
| 3,812,862 A | * | 5/1974 | Bernstein .................. | A41C 1/08 450/154 |
| 5,221,227 A | * | 6/1993 | Michels ............... | A41C 3/0057 2/73 |
| 5,257,419 A | * | 11/1993 | Alexander .............. | A61F 5/028 2/338 |
| 5,537,690 A | * | 7/1996 | Johnson ................... | A41C 1/08 2/44 |

(Continued)

FOREIGN PATENT DOCUMENTS

| | | | |
|---|---|---|---|
| CN | 102697200 A | * | 10/2012 |
| JP | 2003-061994 A | | 3/2003 |

(Continued)

OTHER PUBLICATIONS

Translation of CN-102697200-A (Year: 2012).*
Translation of JP-2013116166-A (Year: 2013).*

*Primary Examiner* — Alireza Nia
*Assistant Examiner* — Samuel B. Lum
(74) *Attorney, Agent, or Firm* — Korus Patent, LLC; Seong Il Jeong

(57) ABSTRACT

A vest-type maternity belt according to the present invention includes: a maternity belt body provided in the shape of a vest; size adjusting VELCRO members configured such that female VELCRO members and a male VELCRO member are fixedly disposed on both sides of the front part of the maternity belt body and a fastening function is provided; hook fastener members configured such that hooks and loops are fixedly and oppositely disposed on both sides of the lower end portion of the front part of the maternity belt body and the abdominal load of the pregnant woman can be borne; and spine correction elastic bands formed as elastic members contained in the back part of the maternity belt body, and configured to support and correct the spine of the pregnant woman.

4 Claims, 3 Drawing Sheets

(58) Field of Classification Search
CPC .... A61F 5/37; A61F 9/02; A61F 9/002; A61F 9/025; A41C 1/00; A41C 1/02; A41C 1/04; A41C 1/08; A41C 1/10; A41C 1/12; A41C 3/00; A41C 3/0028; A41C 3/005; A41C 3/0057; A41C 3/0064; A44B 13/0052; A44B 13/0076; A44B 18/00; A44B 18/0003; A44B 18/0007; A44B 18/0011; A44B 18/0015; A44B 18/0057; A44B 18/0061; A41D 1/02; A41D 1/04; A41D 1/20; A41D 27/00; A41D 2300/326; Y10S 2/02; Y10S 2/03
USPC ................. 602/19; 2/76, 306, 359, 360–363, 2/912–914
See application file for complete search history.

(56) References Cited

U.S. PATENT DOCUMENTS

| 8,113,911 | B1 * | 2/2012 | Hansen | .................... A41D 1/21 450/155 |
| 2015/0040286 | A1 * | 2/2015 | Schultz | .................... A41D 1/00 2/88 |

FOREIGN PATENT DOCUMENTS

| JP | 2010-234041 A | | 10/2010 | |
| JP | 2013116166 A | * | 6/2013 | .......... A47D 13/025 |
| KR | 20-0208604 Y1 | | 1/2001 | |
| KR | 20-2009-0008813 U | | 9/2009 | |

* cited by examiner

VEST-TYPE MATERNITY BELT

TECHNICAL FIELD

The present invention relates to a vest-type maternity belt, and more specifically to a vest-type maternity belt which enables a pregnant woman to spend a secure pregnancy period by allowing the pregnant woman to relieve physical and psychological stress occurring during the pregnancy period, which can protect a pregnant woman and an embryo or fetus, and which can be worn as a fashion coordination item of a pregnant woman.

BACKGROUND ART

Generally, pregnancy and birth started from the advent of humankind, and must continue as long as humankind is present on the earth.

Currently, Korea has been a low-fertility country, and has presented various policies to deal with the serious problem of the lack of future national human resources. However, most policies are limited in that they are support measures after birth.

A typical pregnancy period is 10 months, and is a long period which must be spent by a pregnant woman alone. During a pregnancy period, changes in a mother's body are serious, and a pregnant woman must experience and endure such serious changes.

During such a pregnancy period, a pregnant woman experiences large and small difficulties. In light of the development of the civilization of humankind, consideration for pregnant women is still insufficient.

Accordingly, it is time to make efforts to contemplate the most troubling one of difficulties which are experienced by pregnant women during pregnancy periods from the point of view of the pregnant women and seek a solution thereto.

In particular, in the case of a pregnant woman who is pregnant with a second child after the birth of a first child, the pregnant woman has a hard time because she must pay attention to an embryo or fetus while taking care of the first child. As the pregnancy period passes, changes in her body become serious, and thus the pregnant woman becomes heavier or has slow behavior, thereby making the pregnant woman harder. Furthermore, she cannot easily deal with the active movement of the first child, suffers from difficulty in taking care of the first child, and tends to experience even a psychological fear.

This is a phenomenon which occurs because the pregnant woman has a swelling abdomen and becomes heavier due to the growth of the embryo or fetus. She reaches a state in which it is difficult for her not only to run but also to step forward. Accordingly, she becomes tired from taking care of the first child, and cannot behave freely because she must look for the embryo or fetus.

As described above, a pregnant woman experiences changes in her body during a pregnancy period of 10 months. In particular, a pregnant woman has a swelling abdomen due to the growth of an embryo or fetus, and becomes heavier.

As a result, a pregnant woman suffers from a load applied to her spine due to her swelling abdomen, and sometimes experiences a pain in her spine. Furthermore, a pregnant woman suffers from psychological instability due to serious stress that she experiences due to her downwardly sagging abdomen attributable to an increase in weight whenever she moves.

Moreover, when a pregnant woman goes out to a hospital, part or the like, she has a vague and potential fear that an embryo or fetus is injured by external impact.

Although maternity belts are used for the purpose of compensating for such changes in mothers' bodies, most conventionally used maternity belts are configured to surround abdominal regions. Accordingly, they cannot appropriately bear the abdominal loads of pregnant women, and rather increase pressure to abdominal regions. Furthermore, they are simply added to abdomens, and thus the silhouettes of pregnant women are significantly degraded.

Additionally, a current social environment is in a state in which the use of electronic devices has been popularized in daily life and electronic devices have been widely spread. Accordingly, everyone is in the state of being easily exposed to the risk of electromagnetic waves. In such an environment in which everyone is easily exposed to electromagnetic waves, the tendency for a pregnant woman to be afraid of pregnancy and birth is deepening due to a protective instinct based on maternity regarding an embryo or fetus. This may naturally result in a situation in which women reject pregnancy and birth.

DISCLOSURE

Technical Problem

The present invention has been conceived to overcome and contemplate the above-described problems, and an object of the present invention is to provide a vest-type maternity belt which enables a pregnant woman to spend a secure pregnancy period by allowing the pregnant woman to relieve physical and psychological stress occurring during the pregnancy period, which can protect a pregnant woman and an embryo or fetus, and which can be worn as a fashion coordination item of a pregnant woman.

An object of the present invention is to provide a vest-type maternity belt which is formed in the shape of a vest which can be worn on a body, which enables the size thereof to be adjusted according to the months of pregnancy, which can securely bear the load of an embryo or fetus, and which can securely surround the abdominal region of a pregnant woman in preparation for external impact.

An object of the present invention is to provide a vest-type maternity belt which can securely bear the abdominal load of a pregnant woman in a dual and/or triple manner, which contains a spine correction elastic band so that pain in a spine attributable to the imbalance of a body can be removed and pressure applied to a body can be relieved, which enable the center portion of a vest to be selectively opened and closed via zippers so that the size of the belt can be adjusted according to the months of pregnancy, and which contains an electromagnetic wave shield pad so that a pregnant woman and an embryo or fetus can be protected from electromagnetic waves.

Technical Solution

In order to accomplish the above objects, the present invention provides a vest-type maternity belt, including: a maternity belt body 110 provided in the shape of a vest so that a pregnant woman can wear it on the upper portion of her body; size adjusting VELCRO members 120 configured such that female VELCRO members 121 and a male VELCRO member 122 are fixedly disposed on both sides of the front part of the maternity belt body 110 in vertical lengthwise directions so that the pregnant woman can wear the maternity belt while adjusting the size of the maternity belt body 110 according to her months of pregnancy and such that a fastening function is provided so that her overall abdominal region can be surrounded and protected; hook fastener members 130 configured such that hooks 131 and loops 132 are fixedly and oppositely disposed on both sides of the lower end portion of the front part of the maternity belt body 110 and such that the abdominal load of the pregnant woman can be borne by catching and fastening the hooks 131 onto the loops 132; and spine correction elastic bands 140 formed as elastic members contained in the back part of the maternity belt body 110, and configured to support and correct the spine of the pregnant woman; wherein the hook fastener members 130 are configured such that a female VELCRO strap 191 is provided on the outside of the lower end portion of the front part of the maternity belt body 110 and the loops 132 are coupled and fixedly disposed onto the female VELCRO strap 191 and such that a male VELCRO strap 192 is provided on the inside of the lower end portion of the front part of the maternity belt body 110 and the hooks 131 are coupled and fixedly disposed onto the male VEL-CRO strap 192, thereby increasing the force used to support an abdominal region.

In this case, the vest-type maternity belt may further include zipper opening and closing portions 150 formed to be selectively opened and closed on the center region of the front part of the maternity belt body 110 and configured to adjust the level of pressure applied from the front part to the body by taking account the characteristics of the abdominal region of the pregnant woman based on her months of pregnancy; and the zipper opening and closing portions 150 may be provided on both left and right sides of the maternity belt body 110, and may be configured to be opened in a horizontal direction from the front centerline of the maternity belt body 110, thereby enabling a space regarding the center region of the front part of the maternity belt body 110 to be adjusted.

In this case, the vest-type maternity belt may further include abdominal load bearing elastic bands 160 formed as elastic members contained in both sides of the front part of the maternity belt body 110 and configured to support the abdominal load of the pregnant woman and to pull the abdominal region without sagging downward; and the abdominal load bearing elastic bands 160 may include: an abdominal load bearing band horizontally disposed on the lower end portion of the maternity belt body 110; and abdominal load pulling bands connected to the abdominal load bearing band, disposed in an upper lengthwise direction, and extended up to a shoulder line.

In this case, the vest-type maternity belt may further include an electromagnetic wave shield pad 170 contained in the front part or back part of the maternity belt body 110 or both and configured to protect an embryo or fetus and the pregnant woman from various types of electromagnetic waves; and the electromagnetic wave shield pad 170 may be inserted and disposed between an outer fabric and an inner fabric and provided in a removable form, thereby facilitating washing.

In this case, the female VELCRO members 121 may be located on the outer surface of one side of the front part of the maternity belt body 110 and horizontally disposed at intervals in a vertical lengthwise direction in a plurality of rows, and the male VELCRO member 122 may be located on the inner surface of the other side of the front part of the maternity belt body 110 and vertically disposed in a rectilinear line; and the loops 132 may be located on one side of the outer surface of the front part of the maternity belt body 110 and disposed at intervals in a lateral direction in a plurality of rows, thereby enabling fastening force of the hooks 131 to be adjusted and also increasing abdominal region bearing force.

The loops 182 may be disposed on the female VELCRO members 121 at equal intervals in a plurality of rows; and the hooks 181 may be fixedly disposed on the male VEL-CRO member 122 so as to be caught in the loops 182, thereby increasing abdominal region supporting force.

Advantageous Effects

The present invention provides useful effects in that a pregnant woman is enabled to spend a secure pregnancy period while relieving physical and psychological stress occurring during the pregnancy period, a pregnant woman and an embryo or fetus can be protected, and the belt is formed in the shape of a vest which can be worn on a body so that a pregnant woman can wear the belt as a fashion coordination item.

The present invention provides useful effects in that the size of the belt can be adjusted according to the months of pregnancy, the load of an abdominal region can be securely borne and pulled so that an embryo or fetus can be securely borne, the abdominal region of a pregnant woman can be securely surrounded, and external impact can be prepared for so that a pregnant woman and an embryo or fetus can be protected.

The present invention achieves useful effects in that pain in a spine attributable to imbalance of the body of a pregnant woman can be removed, adjustment based on the months of pregnancy can be performed through the adjustment of the opening and closing of a space via zippers in the center portion of the front part of a vest so that pressure applied to a body can be relieved, and a pregnant woman and an embryo or fetus can be protected from electromagnetic waves.

The present invention provides useful effects in that when a user wears the belt in the case where the user is pregnant with a second child after the birth of a first child, the load of an abdominal region can be borne and pulled so that it is possible to deal with the active movement of the first child while protecting not only the pregnant woman herself but also an embryo or fetus inside her, thereby providing psychological stability.

MODE FOR INVENTION

Preferred embodiments of the present invention will be described below with reference to the accompanying drawings. Through this detailed description, the objects and configurations of the present invention and features based on the objects and the configurations will be sufficiently understood.

Figure 1:
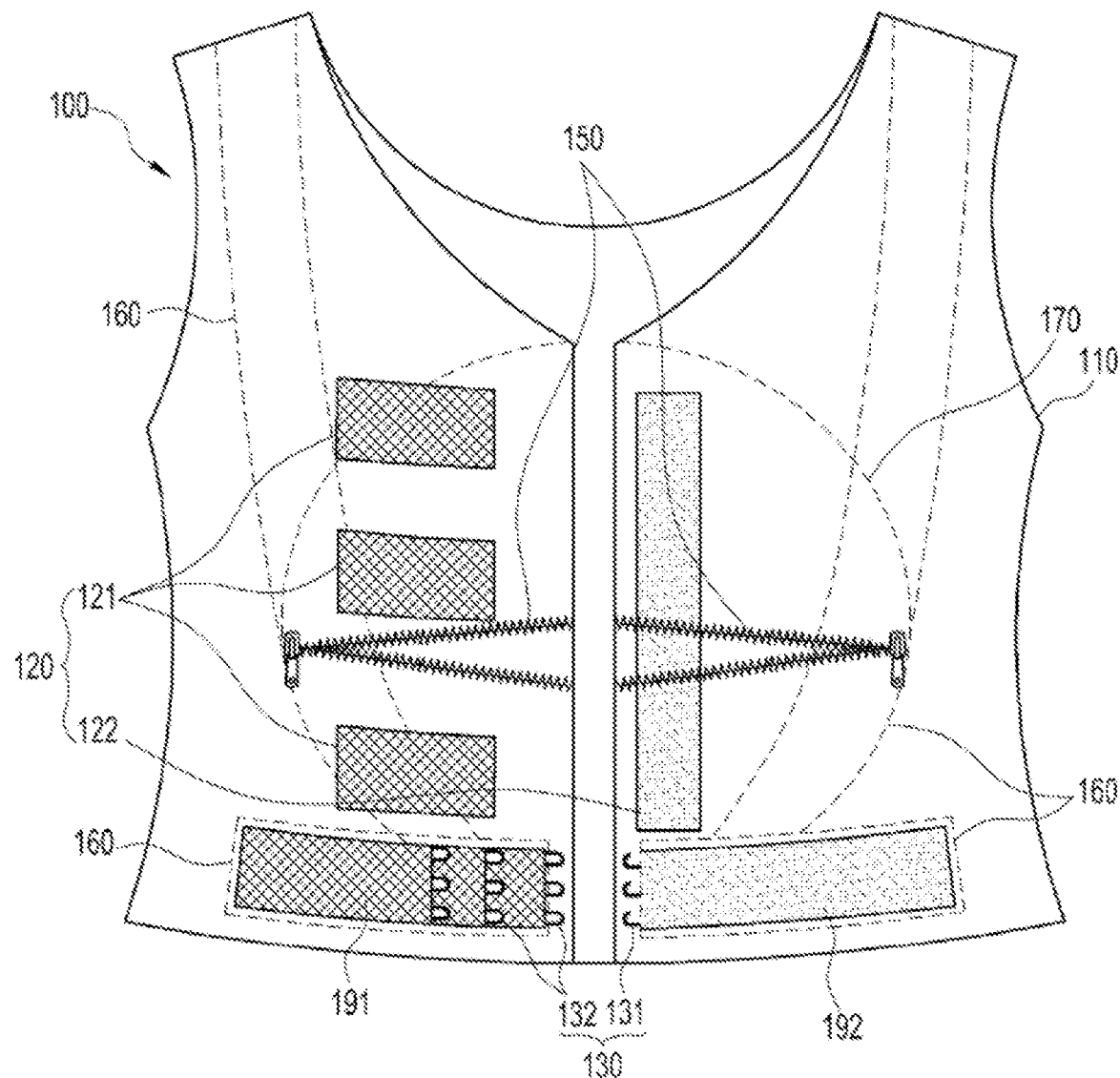
FIG. 1 is a front view illustrating the configuration of a vest-type maternity belt according to an embodiment of the present invention.
Figure 2:
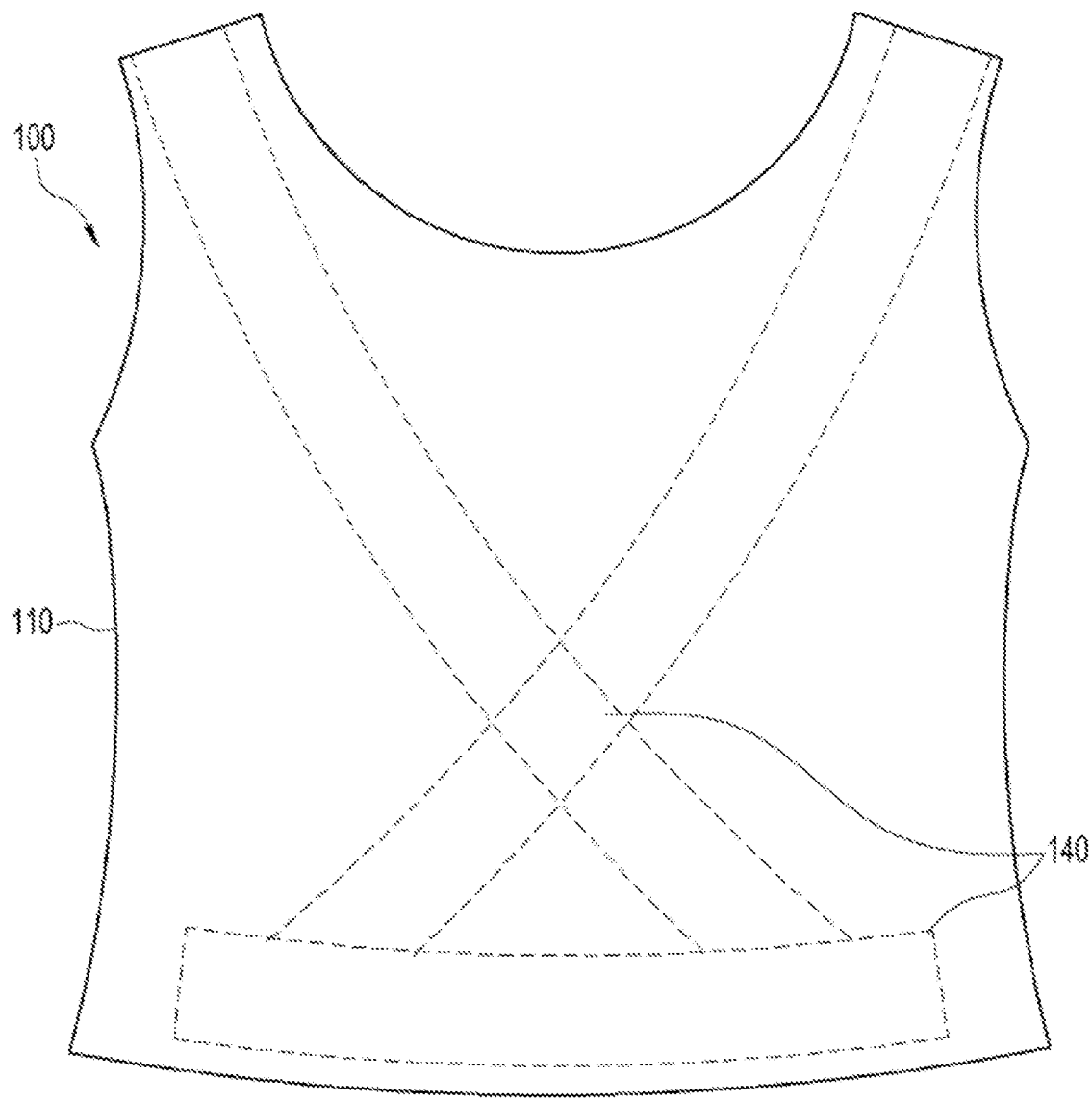
FIG. 2 is a rear perspective view illustrating the vest-type maternity belt according to the embodiment of the present invention.
Figure 3:
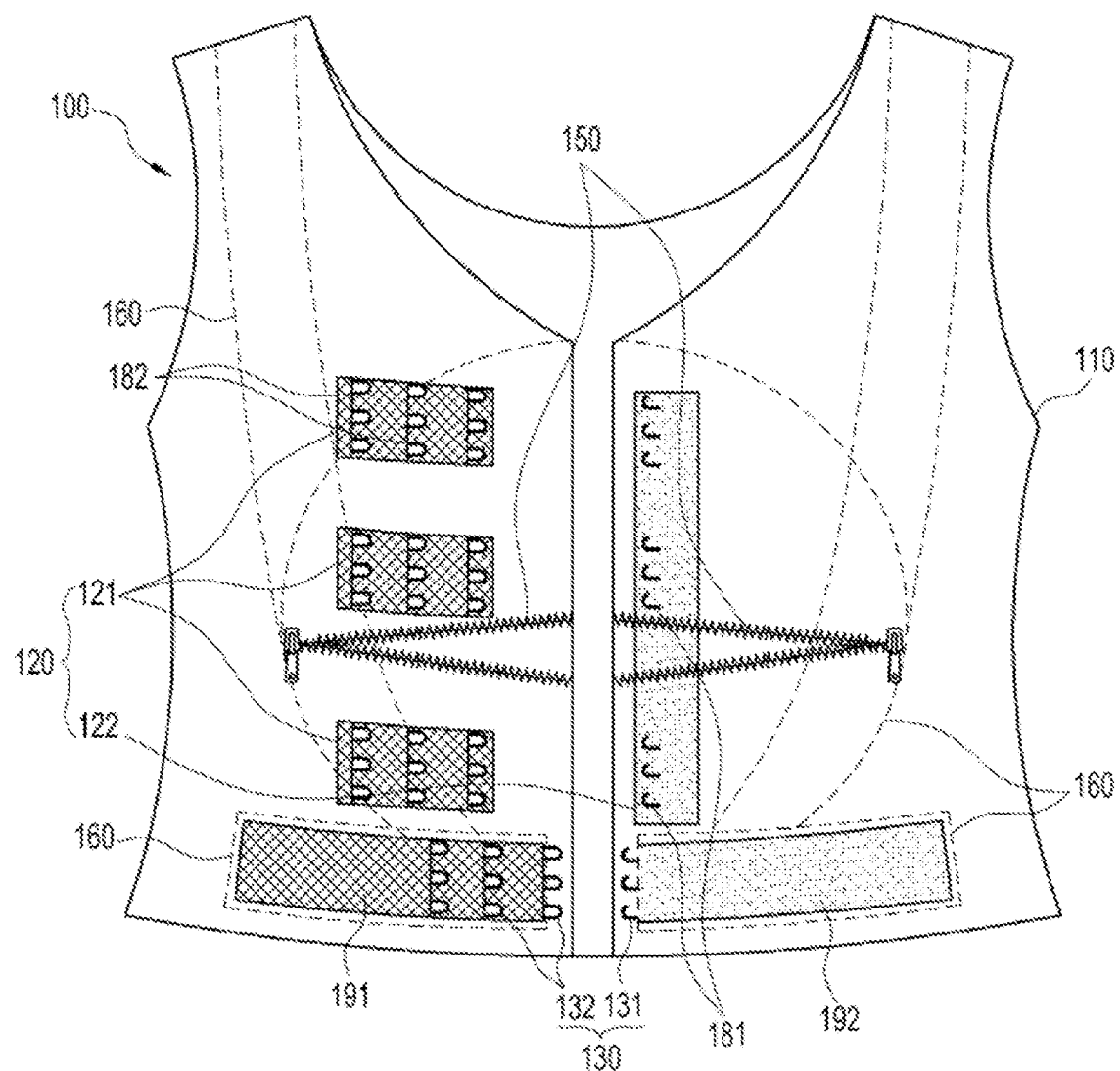
FIG. 3 is a front view illustrating the configuration of a vest-type maternity belt according to another embodiment of the present invention.

As shown in FIGS. 1 to 3, a vest-type maternity belt 100 according to an embodiment of the present invention is configured to include a maternity belt body 110, size adjusting VELCRO members 120, hook fastener members 130, spine correction elastic bands 140, zipper opening and closing portions 150, abdominal load bearing elastic bands 160, an electromagnetic wave shield pad 170, hooks 181 and loops 182, and a female VELCRO strap 191 and a male VELCRO strap 192.

The maternity belt body 110 is provided in the shape of a vest so that a pregnant woman can wear it on the upper portion of her body, and includes an outer fabric and an inner fabric.

In this case, since the maternity belt body 110 is provided in the shape of a vest, a pregnant woman may wear the maternity belt body 110 as a fashion coordination item.

The size adjusting VELCRO members 120 are configured such that female VELCRO members 121 and a male VELCRO member 122 are fixedly disposed on both sides of the front part of the maternity belt body 110, provided in the shape of a vest, in vertical lengthwise directions so that a pregnant woman can wear the maternity belt while adjusting the size of the maternity belt body 110 according to her months of pregnancy and such that a fastening function is imparted to the maternity belt body 110 so that her overall abdominal region can be surrounded and protected.

In other words, the female VELCRO members 121 and the male VELCRO member 122 are a type of fastening members or locking members which gather the front part of the maternity belt body 110 provided in the shape of a vest.

In this case, the female VELCRO members 121 are located on the outer surface of one side (the outer surface of the outer fabric) of the front part of the maternity belt body 110 and horizontally disposed at intervals in a vertical lengthwise direction in a plurality of rows, and the male VELCRO member 122 is located on the inner surface of the other side (the outer surface of the inner fabric) of the front part of the maternity belt body 110 and vertically disposed in a rectilinear line.

In this case, the female VELCRO members 121 have patch shapes having a band structure, and are extended to a predetermined length in a lateral direction so that the location at which the male VELCRO member 122 is attached can be adjusted.

Additionally, as shown in FIG. 3, hooks 181 and loops 182 may be additionally provided on the female VELCRO members 121 and the male VELCRO member 122 constituting the size adjusting VELCRO members 120 in order to increase fastening force and supporting force used to gather the front part of the maternity belt body 110.

In this case, the hooks 181 are coupled and fastened onto the male VELCRO member 122, and the loops 182 are coupled and fastened onto the female VELCRO members 121.

In this case, the loops 182 are disposed on the female VELCRO members 121 at equal intervals in a plurality of rows.

The hook fastener members 130 are configured such that hooks 131 and loops 132 are fixedly and oppositely disposed on both sides of the lower end portion of the front part of the maternity belt body 110 and such that the abdominal load of a pregnant woman can be borne by catching and fastening the hooks 131 onto the loops 132.

In this case, the loops 132 are located on one side of the outer surface of the front part of the maternity belt body 110 provided in the shape of a vest and disposed at intervals in a lateral direction in a plurality of rows, thereby enabling the fastening force of the hooks 131 to be adjusted.

Additionally, the hook fastener members 130 are preferably configured such that the female VELCRO strap 191 is provided on the outside of the lower end portion (the outer surface of the outer fabric) of the front part of the maternity belt body 110 and the loops 132 are coupled and fixedly disposed onto the female VELCRO strap 191 and such that the male VELCRO strap 192 is provided on the inside of the lower end portion (the outer surface of the inner fabric) of the front part of the maternity belt body 110 and the hooks 131 are coupled and fixedly disposed onto the male VELCRO strap 192, thereby further increasing force used to support the load of an abdominal region.

In this case, the hooks 181 and loops 182 coupled onto the size adjusting VELCRO members 120 and the hook fastener members 130 coupled onto the female VELCRO strap 191 and the male VELCRO strap 192 provide a dual structure at their locations, thereby increasing force used to support the abdominal load of a pregnant woman and also providing a synergy effect to the abdominal region supporting force through a vertical matching configuration.

The spine correction elastic bands 140 are elastic members contained in the back part of the maternity belt body 110 (between the outer fabric and the inner fabric), are a configuration configured to support and correct the spine of a pregnant woman.

In this case, as shown in the drawing, the spine correction elastic bands 140 includes: an X band part provided in a lengthwise direction from a shoulder region to a lower side and disposed in an X-shaped structure; and a lower end support band part connected to the lower end portions of the X band part, horizontally disposed, and configured to support a waist region.

The zipper opening and closing portions 150 are formed to be selectively opened and closed on the center region of the front part of the maternity belt body 110 provided in the shape of a vest, and are a configuration configured to adjust the level of pressure applied from the front part to a body by taking account the characteristics of the abdominal region of a pregnant woman based on her months of pregnancy.

In this case, the zipper opening and closing portions 150 are provided on both left and right sides of the maternity belt body 110, and are configured to be opened in a horizontal direction from the front centerline of the maternity belt body 110, thereby enabling a space regarding the center region of the front part of the maternity belt body 110 to be adjusted.

The abdominal load bearing elastic bands 160 are elastic members contained in both sides of the front part of the maternity belt body 110 (between the outer fabric and the inner fabric), and are a configuration configured to support the abdominal load of a pregnant woman and to pull an abdominal region without sagging downward.

In this case, the abdominal load bearing elastic bands 160 are preferably configured to be connected to the spine correction elastic bands 140, and are made of the same material as the spine correction elastic bands 140.

In this case, as shown in the drawings, the abdominal load bearing elastic bands 160 include: an abdominal load bearing band horizontally disposed on the lower end portion of the maternity belt body 110; and abdominal load pulling bands connected to the abdominal load bearing band, disposed in an upper lengthwise direction, and extended up to a shoulder line.

In this case, the abdominal load bearing band of the abdominal load bearing elastic bands 160 is provided inside the front part of the maternity belt body 110.

The electromagnetic wave shield pad 170 may be contained in the front part or back part of the maternity belt body 110 or both, and is a configuration configured to protect an embryo or fetus and a pregnant woman from various types of electromagnetic waves which are generated from WiFi, a smart device, and/or the like.

In this case, the electromagnetic wave shield pad 170 is preferably inserted and disposed between the outer fabric and the inner fabric and provided in a removable form, thereby enabling the electromagnetic wave shield pad 170 to be removed in the case of washing and thus facilitating the washing of the maternity belt 100.

As a result, according to the vest-type maternity belt 100 according to the present invention, which is configured as described above, the belt is formed in the shape of a vest which can be worn on a body so that a pregnant woman can wear the belt as a fashion coordination item, the overall abdominal region of a pregnant woman can surrounded and protected such that the pregnant woman and an embryo or fetus can be protected, the size of the belt can be adjusted in use so that the level of fastening can be adjusted according to the months of pregnancy, the abdominal load of a pregnant woman can be securely borne and pulled, and a pregnant woman and an embryo or fetus can be protected from external impact.

Furthermore, pain in a spine attributable to the imbalance of the body of a pregnant woman can be removed and relieved, a pregnant woman and an embryo or fetus can be protected from electromagnetic waves, and support can be given to a pregnant woman so that the pregnant woman can spend a secure pregnancy period while relieving physical and psychological stress occurring during the pregnancy period.

While the present invention has been described above in conjunction with the specific embodiments, the present invention is not particularly limited by the embodiments disclosed herein and the accompanying drawings. It will be apparent that variations and modifications may be made by those skilled in the art in various manners within the range which does not depart from the technical spirit of the present invention.

The invention claimed is:

1. A vest-type maternity belt, comprising:
   a maternity belt body provided in a shape of a vest so that a pregnant woman can wear it on an upper portion of her body;
   size adjusting coupling members configured such that female coupling members and a male coupling member are fixedly disposed on left and right sides of a front part of the maternity belt body, respectively, in vertical lengthwise directions so that the pregnant woman can wear the maternity belt while adjusting a size of the maternity belt body according to her months of pregnancy and such that a fastening function is provided so that her overall abdominal region can be surrounded and protected;
   hook fastener members configured such that hooks and loops are fixedly and oppositely disposed on left and right sides of a lower end portion of the front part of the maternity belt body, respectively, and such that an abdominal load of the pregnant woman can be borne by catching and fastening the hooks onto the loops;
   spine correction elastic bands formed as elastic members contained in a back part of the maternity belt body, and configured to support and correct a spine of the pregnant woman;
   left and right zipper opening and closing portions formed in a horizontal direction with a predetermined length on left and right sides of a center region of the front part of the maternity belt body, respectively, such that the left and right zipper opening and closing portions are selectively opened and closed and configured to adjust a level of pressure applied from the front part to the body by taking account characteristics of the abdominal region of the pregnant woman based on her months of pregnancy; and
   abdominal load bearing elastic bands formed as elastic members contained in the left and right sides of the front part of the maternity belt body and configured to support the abdominal load of the pregnant woman and to pull the abdominal region without sagging downward, the abdominal load bearing elastic bands and the spine correction elastic bands being made of a same material,
   wherein the hook fastener members are configured such that a female coupling strap is provided on an outside of the lower end portion of the front part of the maternity belt body and the loops are coupled and fixedly disposed onto the female coupling strap and such that a male coupling strap is provided on an inside of the lower end portion of the front part of the maternity belt body and the hooks are coupled and fixedly disposed onto the male coupling strap, thereby increasing force used to support the abdominal region;
   wherein the left and right zipper opening and closing portions are configured to be opened along the horizontal direction from a front centerline of the maternity belt body, thereby enabling a space regarding the center region of the front part of the maternity belt body to be adjusted; and
   wherein the abdominal load bearing elastic bands include:
   an abdominal load bearing band horizontally disposed on the lower end portion of the maternity belt body; and
   abdominal load pulling bands connected to the abdominal load bearing band at lower ends thereof, disposed in an upper lengthwise direction, extended up to a shoulder line, and connected to the spine correction elastic bands at upper ends thereof.

2. The vest-type maternity belt of claim 1, further comprising an electromagnetic wave shield pad contained in the front part or back part of the maternity belt body or both and configured to protect an embryo or fetus and the pregnant woman from various types of electromagnetic waves;
   wherein the electromagnetic wave shield pad is inserted and disposed between an outer fabric and an inner fabric and provided in a removable form, thereby facilitating washing.

3. The vest-type maternity belt of claim 1, wherein:
   the female coupling members are located on an outer surface of one side of the front part of the maternity belt body and horizontally disposed at intervals in a vertical lengthwise direction in a plurality of rows, and the male coupling member is located on an inner surface of a remaining side of the front part of the maternity belt body and vertically disposed in a rectilinear line; and
   the loops are located on one side of an outer surface of the front part of the maternity belt body and disposed at intervals in a lateral direction in a plurality of rows, thereby enabling fastening force of the hooks to be adjusted and also increasing abdominal region bearing force.

4. The vest-type maternity belt of claim 1, wherein:
the loops are disposed on the female coupling members at equal intervals in a plurality of rows; and
the hooks are fixedly disposed on the male coupling member so as to be caught in the loops, thereby increasing abdominal region supporting force.

* * * * *